United States Patent [19]
Vale, Jr. et al.

[11] Patent Number: 6,023,011
[45] Date of Patent: Feb. 8, 2000

[54] CORTICOTROPIN-RELEASING FACTOR OVERPRODUCING TRANSGENIC MICE

[75] Inventors: Wylie W. Vale, Jr., La Jolla, Calif.; Mary P. Stenzel-Poore, Westlinn, Oreg.

[73] Assignee: The Salk Insitute for Biological Studies, La Jolla, Calif.

[21] Appl. No.: 08/068,754

[22] Filed: May 28, 1993

[51] Int. Cl.[7] .............................. C12N 5/00; C12N 15/00; C12N 15/09; C12N 15/63

[52] U.S. Cl. ..................................... 800/18; 800/9; 800/3; 800/25; 435/455; 536/24.1; 536/23.1; 536/23.4; 536/23.51; 536/23.5

[58] Field of Search ................................. 800/2, 18, 9, 3, 800/25; 536/24.1, 23.1, 23.4, 23.5, 23.51; 935/43, 53, 55; 435/455

[56] References Cited

U.S. PATENT DOCUMENTS 5,219,855  6/1993  Saito et al. ............................... 514/252
5,221,778  6/1993  Byrne et al. ............................... 800/2

OTHER PUBLICATIONS

Hoha et al. 1991. Life Sciences 48: 1483–1491.
Low et al. 1986. J. Biol. Chem. 261(34): 16260–16263.
Sutton et al. 1982. Nature 297: 331–333.
Thompson et al. 1987 Annals of The New York Academy of Sciences 512: 1–11.
Palmiter et al. 1983. Science 222: 809–814.
Schmid et al. 1991. Development 113:857–865.
Cameron et al., "Tissue Distribution of CRF Over–Expression in Transgenic Mice," *Society for Neuroscience Abstracts*, vol. 17., No. 434.4 (1991).
Stenzel–Poore and Vale, "Corticotropin–Releasing Factor (CRF) Transgenics: A Mouse Model of Chronic CRF and Glucocorticoid Overproduction which Mimics Cushing's Syndrome," *Journal of Cellular Biochem.* 15A:203 (1991).
Stenzel–Poore et al., "Development of Cushing's Syndrome in Corticotropin–Releasing Factor Transgenic Mice," *Endocrinology* 130:3378–3386 (1992).

*Primary Examiner*—Deborah Crouch
*Assistant Examiner*—Jill D. Martin
*Attorney, Agent, or Firm*—Gray Cary Ware & Freidenrich; Stephen E. Reiter; David F. Kleinsmith

[57] ABSTRACT

In accordance with the present invention, there are provided CRF overproducing transgenic mice which exhibit endocrine abnormalities involving the hypothalamic-pituitary-adrenal axis, such as elevated plasma levels of ACTH and glucocorticoids. The transgenic mice of the present invention represent a genetic model of CRF overproduction, providing a valuable tool for investigating the long term effects of CRF excess and dysregulation in the central nervous system.

7 Claims, 4 Drawing Sheets

CORTICOTROPIN-RELEASING FACTOR OVERPRODUCING TRANSGENIC MICE

ACKNOWLEDGEMENT

This invention was made with Government support under Grant Numbers DK26741, DK08385, TWO-4397, AA07456/06420 awarded by the National Institutes of Health. The Government has certain rights in the invention.

FIELD OF THE INVENTION

The present invention relates to the generation of transgenic mice and uses therefor.

BACKGROUND OF THE INVENTION

Corticotropin-releasing factor (CRF) is a 41-residue hypothalamic peptide which stimulates the secretion and biosynthesis of pituitary ACTH leading to increased adrenal glucocorticoid production. CRF was originally isolated and characterized on the basis of its role in this hypothalamic-pituitary-adrenal axis (HPA) [Vale et al., Science Vol. 213:1394–1397 (1981)]. More recently, however, it has been found to be distributed broadly within the central nervous system (CNS) as well as in extra-neural tissues such as the adrenal glands and testes [Swanson et al., Neuroendocrinology Vol. 36:165–186 (1983); Suda et al., J. Clin. Endocrinol. Metab. Vol. 58:919–924 (1984; Fabbri and Dufau, Endocrinology Vol. 127:1541–1543 (1990)], where it may also act as a paracrine regulator or neurotransmitter.

In addition to its critical role of mediating HPA axis activation, CRF has been shown to modulate behavioral changes that occur during stress response. Many of these behavioral changes have been shown to occur independently of HPA activation in that they are insensitive to dexamethasone treatment and hypophysectomy [Britton et al., Life Sci. Vol. 38:211–216 (1986); Britton et al., Life Sci. Vol. 39:1281–1286 (1986); Berridge and Dunn, Pharm. Bioch. Behav. Vol. 34:517–519 (1989)]. In addition, direct infusion of CRF into the CNS mimics autonomic and behavioral responses to a variety of stressors [Sutton et al., Nature Vol. 297:331–333 (1982); Brown and Fisher, Brain Res. Vol. 280:75–79 (1983); Stephens et al., Peptides Vol. 9:1067–1070 (1988); Butler et al., J. Neurosci. Vol. 10:176–183 (1990)]. Furthermore, peripheral administration of CRF or the CRF antagonist, α-helical CRF 9-41, failed to effect these changes, thus supporting a central role for CRF in such functions.

Central administration of CRF in rodent animal models produces effects that correlate with a state of anxiety such as a reduction in willingness to investigate unfamiliar surroundings [Sutton et al., supra; Sherman and Kalin, Pharm. Biochem. Behav. Vol. 26:699–703 (1987); Berridge and Dunn, supra; Butler et al., supra], decreased sleep [Sherman and Kalin, supra], enhanced fear responses [Sutton et al., supra; Butler et al., supra], decreased food consumption [Morely and Levine, Life Sci. Vol. 31:1459–1464 (1982)] and suppressed sexual behavior [Sirinathsinghji et al., Nature Vol. 305:232–235 (1983)]. These changes are similar to behavioral changes observed upon exposure to acute and chronic stressors, and resemble changes that occur in human affective disorders such as the symptom complex characteristic of major depressive disorder, panic disorder and anorexia nervosa [Kaye et al., J. Clin. Endocrinol. Metab. Vol. 64:203–208 (1987); Gold et al., N. Engl. J. Med. Vol. 319:413–420 (1988); Kathol et al., Psych. Clin. N. Amer. Vol. 22:335–348 (1988); Nemeroff, C. B., Pharmacpsychiat Vol. 21:76–82 (1988)].

Currently, a great deal of interest in CRF has been generated in connection with the pathophysiology of mental illness. For example, CRF hypersecretion has been linked to some individuals diagnosed with major depression [Nemeroff et al., Science Vol. 226:1342–1344 (1984)]. While all studies do not support the suggestion that cerebrospinal fluid CRF levels are altered in this group of individuals, most researchers agree that HPA axis responsivity in these individuals is abnormal. Indeed, a large portion of individuals diagnosed with depression have elevated cortisol levels [Roy-Byrne et al., Am. J. Psychiatry Vol. 143:896–899 (1987); Kling et al., J. Clin. Endocrinol. and Metab. Vol. 72:260–271 (1991)]. Moreover, in major depression [Holsboer et al., N. Engl. J. Med. Vol. 311:1127 (1984)] and panic disorder [Roy-Byrne, supra] CRF administration results in a blunted ACTH response, suggesting that the pituitary is properly restrained, presumably by the negative feedback effect of elevated levels of glucocorticoids. In view of these findings, it has been suggested that the hypercortisolism in major depression is due to abnormal CRF secretion within the CNS [Gold et al., Psychiat. Clinics of N. Amer. Vol. 11:327–335 (1988)].

In order to more fully investigate the role of abnormal CRF secretion within the CNS, it would be desirable to have available animal models with which to study the effects of CRF hypersecretion.

BRIEF DESCRIPTION OF THE INVENTION

In accordance with the present invention, we have developed a transgenic mouse model exhibiting chronic CRF hypersecretion. These animals express high levels of ACTH and corticosterone throughout their life span and develop a Cushing's syndrome phenotype due to excess glucocorticoid production.

Although transgenic animals show normal plasma levels of CRF, numerous central nervous system sites show elevated CRF gene expression. The fact that these animals show chronic hypersecretion of CRF and thus, hyperactivation of the pituitary-adrenal axis, makes them a good model to investigate the role of CRF in long-term behavioral changes, particularly with respect to anxiogenic effects.

As described in greater detail herein, the hypothesis that persistent central CRF hypersecretion produces behavior characteristic of anxiety was tested. Measurements of anxiety were made using an Elevated Plus-Maze, a test that is based on the natural aversion of rodents for open spaces [Pellow et al., J. Neurosci. Methods Vol. 14:149–167 (1985); Lister, R. G., Psychopharmacology Vol. 92:180–185 (1987)]. In addition, the effect of exposure to an unfamiliar (novel) environment on locomotor activity was assessed. The effect of social aggression on the performance of CRF transgenics was also examined in order to determine the reactivity of this animal model to a psychological stressor. Finally, to test whether brain CRF plays a role in mediating behavior characteristic of anxiety among CRF transgenics, the stress protective actions of the centrally administered CRF antagonist, α-helical CRF 9-41, was examined.

mice and of pre-stressed control (●; n=6) or CRF transgenic (■; n=7) mice placed individually for 30 minutes in novel photocell cages. * p<0.05 vs. untreated CRF transgenic group; ** p<0.01 vs. prestressed CRF transgenic mice over a 5 minute test on the elevated plus-maze.

Figure 3A:
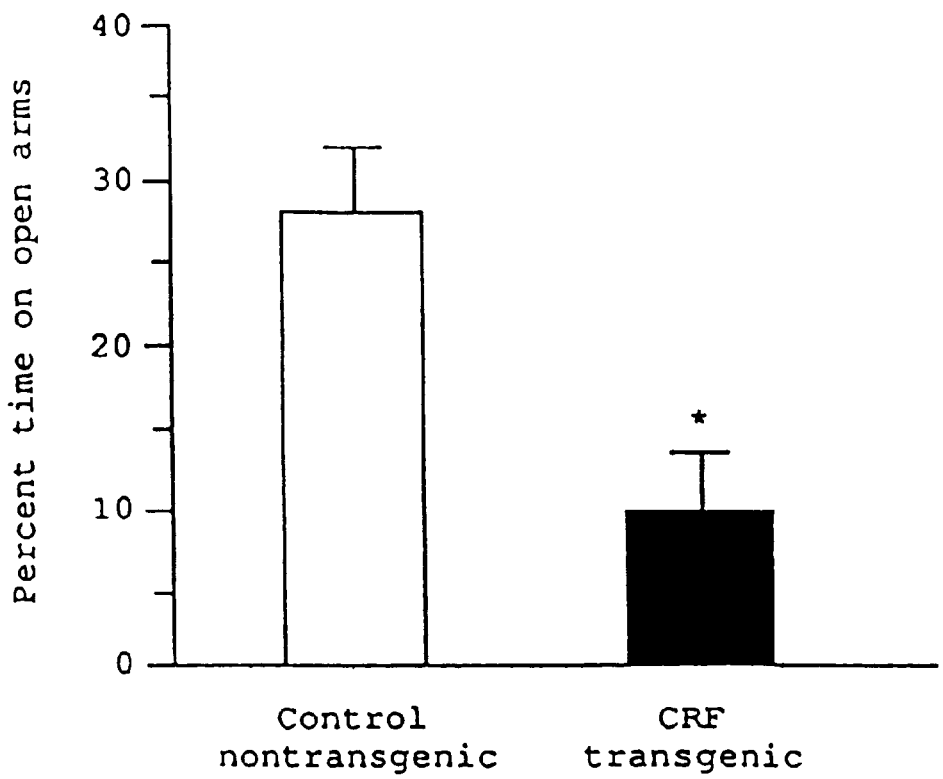
Figure 3B:
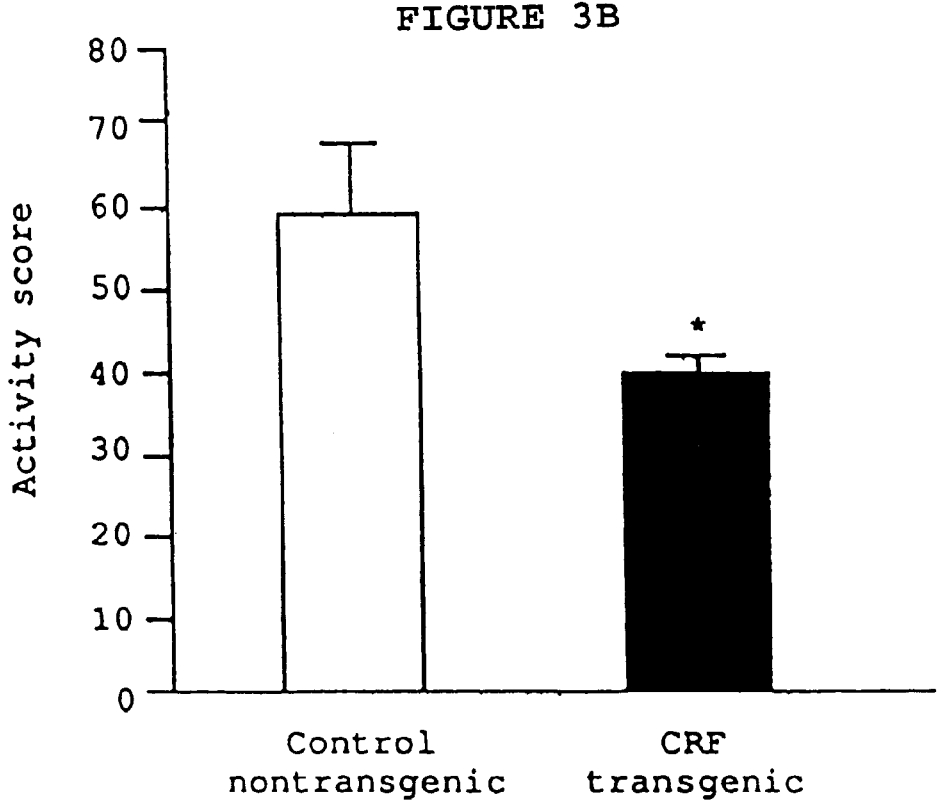

FIGS. 3A and 3B present the mean (±SEM) percent of time spent on the open arms (FIG. 3A) and overall activity (FIG. 3B) of control (n=8) or CRF transgenic (n=10) mice over a 5 minute test on the elevated plus-maze. * p<0.05.

Figure 4A:
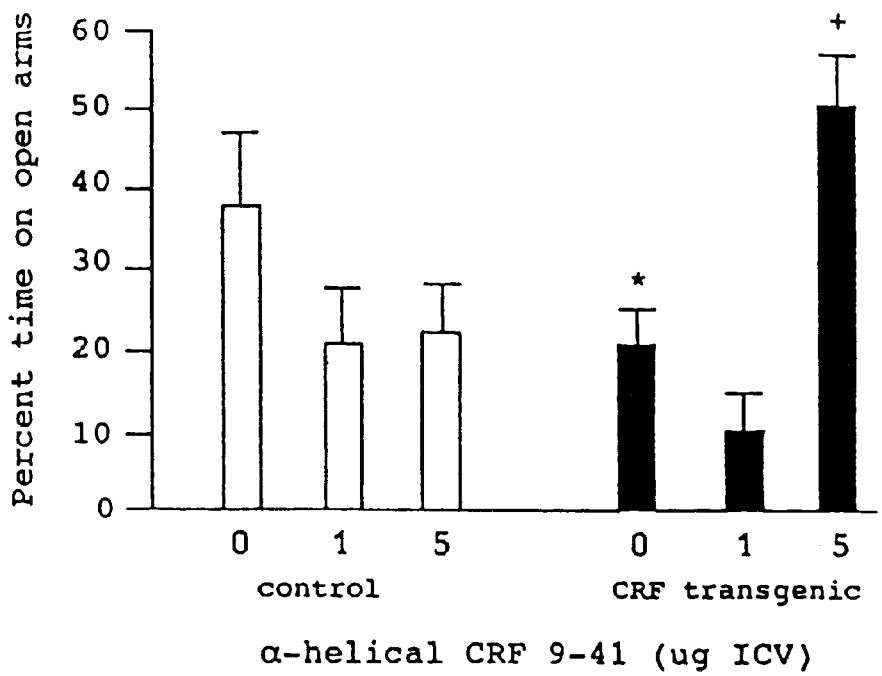
Figure 4B:
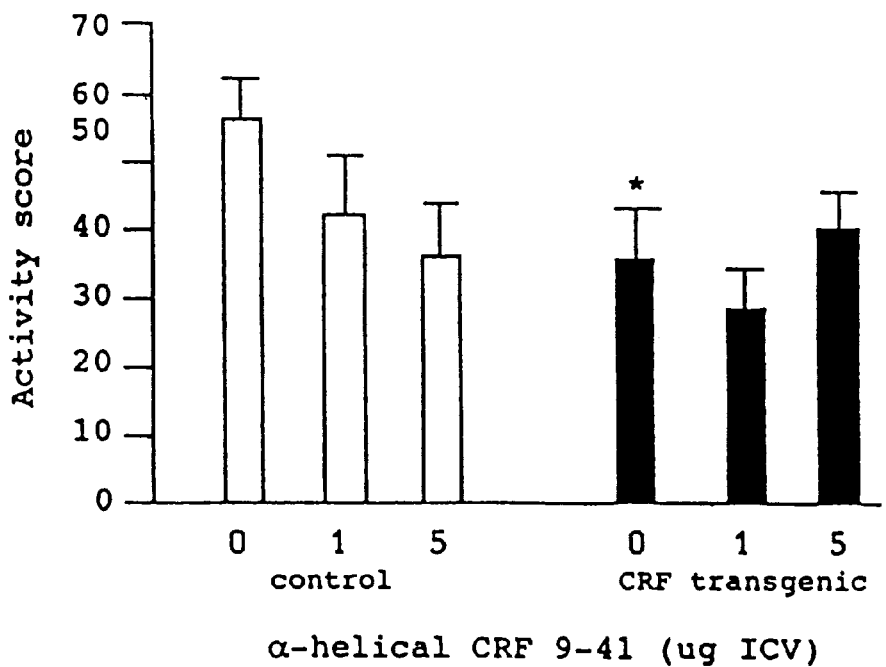

FIGS. 4A and 4B present the mean (±SEM) percent of time spent on the open arms (FIG. 4A) and overall activity (FIG. 4B) during a 5 minute test on the elevated plus-maze following pre-treatment with CRF antagonist of both control (0 $\mu$g pre-treatment, n=7; 1 $\mu$g, n=5; 5 $\mu$g, n=5) and CRF transgenic (0 $\mu$g pre-treatment, n=7; 1 $\mu$g, n=5; 5 $\mu$g, n=6) mice. * p<0.05 vs. vehicle-treated control groups; +p<0.05 vs. vehicle-treated CRF transgenic group.

DETAILED DESCRIPTION OF THE INVENTION

In accordance with the present invention, there are provided transgenic mice containing exogenous DNA encoding corticotropin releasing factor (CRF). Exogenous DNA employed in the practice of the present invention comprises the rat CRF gene under the expression control of either an inducible promoter (e.g., the mouse metallothionein (MT) promoter), or a constitutive promoter.

CRF genes employed in the practice of the present invention may be obtained by isolating them from genomic sources, by preparation of cDNAs from isolated mRNA templates, by direct synthesis, or by some combination thereof. The published sequences of numerous CRF genes greatly facilitates obtaining a gene encoding CRF, and this invention is not limited to the use of any particular gene. However, the rat CRF gene is presently preferred.

To be expressed, the structural gene must be coupled to a promoter in a functional manner, i.e., operably associated therewith. If a constitutive promoter is used, a viral promoter, such as the SV40 early promoter, is preferred. The MT promoter, while often referred to as an "inducible" promoter, can alternatively be described as "semi-constitutive" since it is "on" all of the time, even though its activity is boosted by heavy metal ions. Such promoters, as well as pure inducible promoters, may also be used. Promoter/regulatory sequences may be used to increase, decrease, regulate or target expression to certain tissues or to certain stages of development. The promoter employed need not be a naturally occurring promoter.

The CRF gene may be introduced by zygote microinjection, as described below. Alternatively, the CRF gene may be introduced into non-germline cells (somatic cells) in a fetal, new born, juvenile or adult animal by retroviral vector mediated genetic transformation of somatic cells of one or more tissues within the animal.

The widespread distribution of CRF in brains of normal animals has lead to a heightened interest in the role CRF plays in regulating and integrating complex behavior [Swanson et al., supra; Imaki et al., Brain Res. Vol. 496:35–44 (1989); Imaki et al., Brain Res. Vol. 547:28–36 (1991)]. The relative importance of CRF located in distinct brain regions is unclear, although CRF injection into specific sites, such as the locus coeruleus (Butler et al., supra) and amygdala [Weiss et al., Brain Res. Vol. 372:345–351 (1986); Liang and Lee, Psychopharmacology Vol. 96:232–236 (1988)] have been implicated in effecting distinct behavioral responses. CRF expression in the transgenic model described herein is clearly elevated in a number of sites in the brain, although peripheral plasma levels of CRF do not appear to be elevated. The transgenic mice of the invention display markedly elevated levels of CRF mRNA in nearly all areas where expression is shared in common with controls. In addition, CRF transgenic mice of the invention exhibit prominent levels of mRNA expression in some regions believed to be sites of CRF expression in the rat, whereas CRF was not detectable in such regions in control mice. Regions where mRNA expression was observed in the transgenic mice includes the supraoptic and dorsomedial nuclei of the hypothalamus, lateral hypothalamic area, substantia innominata, vestibular complex, and the lateral reticular nucleus. Moreover, a number of regions not previously identified as sites of CRF expression contain robust mRNA levels in the transgenic mice. Regions where such mRNA expression was observed include the arcuate nucleus of the hypothalamus, the subfornical organ, lateral habenula, the granule cell layer of the dentate gyrus, the dorsal subiculum, and the deep nuclei of the cerebellum.

Daily, repeated administration of CRF has been employed as a means of modeling the chronic state of CRF activation reported to accompany affective and appetitive psychopathology in human clinical populations [see, for example, Hotta et al., Life Sci. Vol. 48:1483–1491 (1991)]. By following this course for several days (or weeks), one can observe diminished weight gain, hypogonadism and persistent hypothalamic-pituitary-adrenal axis activation, which resembles the pattern of psychiatric symptomatology observed in depression or anorexia nervosa. This relation is supported by the present data in which animals with an intrinsic overproduction of CRF exhibit unprovoked hyperactivity to environmental stressors. Furthermore, while these animals have a Cushing's-like phenotype associated with glucocorticoid excess, the present state of anxiety can be attributed to neurotropic actions of CRF within the brain since the enhanced emotionality of the transgenic mice was reversed with a centrally administered CRF receptor antagonist. Hence, this new animal model is well suited for testing neurogenic hypotheses in the etiology of human affective disorders.

Because pituitary ACTH and hypothalamic paraventricular CRF expression is suppressed by glucocorticoids, [Jingami et al, Endocrinology Vol. 117:1314–1320 (1985)] it was unclear whether long term overproduction of CRF by transgenic mice would lead to the development of ACTH-dependent Cushing's syndrome in these animals. In addition, regulatory mechanisms, such as desensitization of CRF receptors, might also modulate the effects of excess CRF production. However, as described herein, a transgenic animal model exhibiting chronic CRF expression has been developed, leading to the development of a Cushing-like syndrome in mice. These animals show elevated CRF expression due to the presence of a rat CRF transgene, which results in chronic pituitary stimulation of ACTH release and elevated glucocorticoid levels. In addition, animals that express the transgene display physical features found among patients with Cushing's syndrome, such as obesity, hair loss, thin skin, muscle wasting, and reduced fertility. Several of these features appear to be due in part to increased circulating corticosterone levels, since adrenalectomized transgenic animals revert to a normal phenotype with respect to hair and skin changes within a month after adrenalectomy.

Treatment with zinc to induce higher expression of the CRF transgene did not change basal corticosterone levels, which may indicate that CRF stimulation of ACTH and, consequently, corticosterone was maximal in this setting or that the regions of expression of the CRF transgene were insensitive to metal induction. Since transgene expression was not compared in the absence and presence of metal induction, it is not known whether the MT-CRF construct in this line is sensitive to such treatments. However, it appears that treatment with zinc did not result in detectable expression of the transgene in several regions where it was expected to occur, such as liver and kidney. Although peripheral plasma CRF levels were not detectably elevated in the transgenics, CRF gene expression in several brain regions was increased, which presumably leads to increased ACTH and corticosterone levels in these animals.

Excess production of CRF has been implicated in the development of corticotrope hyperplasia and microadenoma formation [Cary et al., N. Engl. J. Med. Vol. 311:13–20 (1984); Kreiger, D. T., Endocr. Rev. Vol. 4:22–43 (1983); Gertz et al., Endocrinology Vol. 120:381–388 (1987)]. CRF transgenics were not found to have increased numbers of ACTH-staining cells in the pituitary, nor was a difference in pituitary weight noted among the transgenics. It is possible that changes in corticotrope number may only become apparent in much older transgenic animals or upon removal of glucocorticoid feedback.

CRF expression in transgenic mice was detected in all known sites of endogenous CRF expression. In most of the regions, the level of CRF is elevated in the transgenics compared with that in control animals. Although no CRF was detected in the principal sites of normal MT gene expression (liver and kidney), CRF was found in seminiferous tubules, where MT expression is under unique cadmium-insensitive regulation [Swapan et al., Mol. Endocrinol. Vol. 5:628–636 (1991)]. Thus, MT-CRF gene expression may be influenced by the MT promoter in the seminiferous tubules. CRF expression may occur normally in the pituitary, either at low levels or under specific conditions, and the presence of the transgene amplifies that potential to a level high enough to allow detection. The fact that CRF has been detected in normal rat pituitaries by Northern blot analysis is consistent with this possibility [Thompson et al., Mol. Endocrinol. Vol. 1:363–370 (1987)].

Overall, the majority of sites of CRF transgene expression are normal sites of endogenous expression, which suggests that gene elements carried within the CRF-coding region or intron may be directing tissue-specific expression of the CRF hybrid transgene. Very few transgenes that employ the MT promoter fail to express in the liver [Kelley et al., Mol. Cell Biol. Vol. 8:1821–825 (1988)], although novel cell distribution patterns have been reported that appear to result from the combined influence of both genetic components of the fusion gene [Swanson et al., Nature Vol. 317:363–366 (1985)]; [Russo et al., Neuron Vol. 1:311–320 (1988)]. In particular, ectopic neuronal expression has been reported from chimeric transgenes employing the MT promoter; however, the pattern of expression did not appear to be a unique property of the MT promoter alone, since not all MT fusion genes were expressed in neuronal sites [Russo et al. supra]. It is conceivable that novel sites of CRF expression in the transgenics may represent enhancement of expression normally below the level of detection.

The sparse expression of the transgene in peripheral sites could explain the observation that circulating CRF levels are not elevated in the transgenics. Most brain regions considered to be normal sites of CRF expression showed increased CRF hybridization in transgenic brains. One notable exception to this is the strength of the hybridization signal in the paraventricular nucleus of the hypothalamus using a riboprobe that detects both endogenous CRF and the transgene. This may reflect the fact that endogenous CRF expression in the paraventricular nucleus exhibits marked glucocorticoid down-regulation, while extrahypothalamic areas, such as olfactory bulb, midbrain cerebral cortex, and brain stem, have been found to be relatively insensitive to perturbations in corticosteroid titers [Imaki et al., J. Neurosci. Vol. 11:585–599 (1991)].

While there is limited expression in peripheral sites, the transgene is expressed in brain regions that could provide CRF stimulation to ACTH-producing cells in the pituitary, and thereby influence the development of the Cushing's phenotype. In addition to the CRF-containing cells located in the pituitary itself, the paraventricular nucleus, the arcuate nucleus, and the supraoptic nuclei in the hypothalamus are each capable of contributing to the CRF content of the hypophyseal-portal vasculature, which could provide chronic CRF stimulation of pituitary ACTH secretion in the transgenic animals. Thus, increased levels of CRF mRNA at one or more sites in the hypothalamus and pituitary in these animals may be responsible for the elevated ACTH and glucocorticoid levels detected in plasma. Moreover, the finding that CRF is expressed in the pituitary provides a plausible route of paracrine or autocrine regulation of ACTH production by corticotropes. In addition, recent evidence obtained from normal animals indicates that the adrenal gland may modulate glucocorticoids via local ACTH production from adrenal sources [Jones and Edwards, J. Physiol. Vol. 430:25–36 (1990); Andreis et al., Endocrinology Vol. 128:1198–1200 (1991)]. The fact that CRF transgene expression occurs in the adrenal gland in the transgenics may provide an additional mechanism for paracrine regulation of glucocorticoid production that would not necessarily lead to elevations in plasma CRF, but could result in increased local CRF levels and thereby effect ACTH and corticosterone production.

The transgenic mice described herein provide an opportunity to investigate the physiological consequences of overproduction of a central neuropeptide, with numerous effects that modulate behavioral, autonomic, and neuroendocrine functions. The animals display a tissue distribution of CRF expression that should yield exaggerated autocrine and paracrine stimulation. In addition to serving as a novel model of Cushing's disease, CRF transgenic mice may provide useful animal models of clinical depression, anorexia nervosa, and susceptibility to immune dysfunction; all syndromes postulated to involve alterations in central or peripheral CRF systems [Gold et al., N. Engl. J. Med. Vol. 319:413–420 (1988); Kaye et al., J. Clin. Endocrinol. Metab. Vol. 64:203–208 (1987); Sternberg et al., Proc. Natl. Acad. Sci. USA Vol. 86:477–4775 (1989)].

In accordance with another embodiment of the present invention, there is provided a method for treating a subject suffering from anxiety, said method comprising modulating the expression and/or activity of CRF in said subject. Such modulation can be accomplished in a variety of ways, e.g., the activity of CRF can be modulated by administering an effective amount of a CRF antagonist to the subject; or the expression of CRF can be modulated by administering an effective amount of CRF antisense RNA to the subject, and the like.

For the above-contemplated administration, the modulating compounds can be incorporated into a pharmaceutically acceptable formulation for administration. Those of skill in the art can readily determine suitable dosage levels to be used.

As employed herein, the phrase "suitable dosage levels" refers to levels of treating compound sufficient to provide circulating concentrations high enough to alter CRF expression and/or activity. Such a concentration typically falls in the range of about 10 nM up to 2 µM; with concentrations in the range of about 100 nM up to 200 nM being presently preferred.

In accordance with a particular embodiment of the present invention, compositions to be administered are incorporated into a pharmaceutically acceptable carrier. Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

In accordance with yet another embodiment of the present invention, there is provided a method of screening for compounds useful in the treatment of Cushing's syndrome, said method comprising administering test compound(s) to a transgenic mouse of the invention, and monitoring for improvement in symptoms characteristic of Cushing's syndrome.

In accordance with yet another embodiment of the present invention, there is provided a method of screening for compounds useful in the treatment of anxiety, said method comprising administering test compound(s) to a transgenic mouse of the invention and monitoring for improvement in symptoms characteristic of anxiety.

The transgenic animals of the invention can also be used as a source of cells for cell culture. Cells from the animals may advantageously exhibit desirable properties of both normal and transformed cultured cells; i.e., they will be normal or nearly normal morphologically and physiologically, but can, like cells such as NIH3T3 cells, be cultured for long, and perhaps indefinite, periods of time. Further, where the promoter sequence controlling transcription of the recombinant gene sequence is inducible, cell growth rate and other culture characteristics can be controlled by adding or eliminating the inducing factor.

The invention will now be described in greater detail by reference to the following non-limiting examples.

MATERIALS AND METHODS

Animals

CRF transgenic mice were generated by microinjection of a metallothionein-CRF (MT-CRF) gene construct, prepared as follows. The rat genomic CRF gene [see Thompson et al., Molec. Endocrinol. Vol. 1:363–370 (1987)] extending from the Asp718 site in the 5'-untranslated region to the EcoRI site in the 3'-untranslated region (1.7 kilobase pair (kbp) fragment) was used in construction of the fusion gene. The rat CRF gene was digested with the restriction enzymes EcoRI and Asp718, followed by a fill-in reaction with Klenow fragment. The blunt end fragment was ligated into the SmaI site of a plasmid containing the 5' regulatory region of the mouse metallothionein-1 (MT-1) gene (1.8 kbp) [Palmiter et al., Science Vol. 222:809–814 (1983)] and the 3' untranslated region of the human growth hormone gene (0.65 kbp), which contains a polyadenylation signal sequence [DeNoto et al., Nucl. Acids Res. Vol. 9:3719–3730 (1981)]. The MT-CRF gene was prepared for microinjection by isolating a 4.1-kbp EcoRI fragment containing the MT-CRF fusion gene, which was purified by sucrose gradient centrifugation. The fragment was microinjected into the male pronucleus of fertilized eggs (B6/SJL), and the injected eggs were transplanted to pseudopregnant foster mothers following standard procedures [see, for example, Brinster et al., Proc. Natl. Acad. Sci. USA Vol. 82:4438–4442 (1985)]. To identify transgenic founder animals, tail DNA from offspring was screened by standard tail dot blot analyses using a $^{32}P$ randomly labeled 0.65-kbp human GH 3'-fragment as a probe. Offspring of founder mice were screened using the polymerase chain reaction (PCR) and transgene-specific primers to amplify tail DNA. Primers complementary to the CRF transgene carboxyl region:

5'-ACAGGAAACTGATGGAGATTATC-3'; SEQ ID NO:1 and the human GH gene:

5'-TGGTGGGCACTGGAGTGGCAACT-3'; SEQ ID NO:2 were employed. PCR reactions were performed in 100-µl volumes in 50 mM KCl, 10 mM Tris-HCl (pH 8.3), 1.5 mM MgCl, and 2.5 U Taq polymerase (Cetus Corp., Emeryville, Calif.). The following PCR conditions were used: 1 cycle at 95° C. (5 min), 35 cycles at 95° C. (1 min), 55° C. (2 min), and 72° C. (2 min), terminating with 1 cycle at 72° C. for 10 min.

A single transgenic founder male was used as the source of this transgenic line and thus all animals are descendant offspring. Adult male mice (transgenic and nontransgenic littermate controls) aged 2–9 months and weighing 25–30 gm were housed singly in a pathogen-free transgenic facility. Mice were given rodent chow and water ad libitum and kept on a 12 hour light/dark schedule with lights on from 0600 to 1800.

Blood Collection and Hormone Analyses

To obtain baseline hormone levels, plasma was obtained by retroorbital eye bleeding from animals that were housed individually in covered cages. Blood was collected at 0700 h within 45 sec of initial disturbance of the cage, and samples were immediately placed on ice into tubes containing EDTA. Plasma was stored at −20° C. until assayed. Corticosterone levels were measured by RIA, using a rat/mouse [$^{125}I$] corticosterone RIA kit (ICN Biomedicals, Costa Mesa, Calif.). Control animals were nontransgenic littermates or nontransgenic age- and sex-matched animals. Founder animals were bled before zinc treatment (25 mM $ZnSO_4$ in the drinking water) and again 1 month later to determine whether corticosterone levels were sensitive in induction of the transgene by metal.

Basal ACTH levels were measured using a human ACTH two-site immunoradiometric assay (Nichols Institute, San Juan Capistrano, Calif.) with rat ACTH (1–39) as the standard.

Experiments involving animals were performed in accordance with the NIH guidelines for care and use of laboratory animals.

RNA Analyses

Tissue was obtained from mice treated with $ZnSo_4$ (5 mg/kg, sc) 18 h before collection and frozen at −70° C. until use. Total RNA was isolated by guanidinium isothyocyanate-cesium chloride centrifugation, as described by [Chrigwin et al., Biochemistry Vol. 18:5294–5299 (1979)]. Total RNA (20 µg) was electrophoresed in 1.2% agarose-2.2 M formaldehyde gels, blotted, and hybridized with a $^{32}P$-labeled CRF antisense riboprobe, as described by [Imaki et al., supra]. For PCR analyses, total RNA from transgenic animals and control littermates was treated with DNAse (1 U/µg) twice at 37° C. for 15 min before reverse transcription. DNAse was removed by treating the samples with proteinase-K (50 µg in 0.1% sodium dodecyl sulfate) for 15 min at 37° C., followed by phenol-chloroform extraction and ethanol precipitation of the RNA. RNA (3 µg) was reverse transcribed at 37° C. for 1 h using poly(dt) for cDNA priming and reverse transcriptase (avian myeloblastosis virus; 4 U/μg; Life Sciences, St. Petersburg, Fla.). To control for potential false positive amplification of contaminating genomic DNA, duplicate RNA samples without reverse transcriptase were incubated in parallel with the cDNA reactions, followed by PCR amplification. cDNA reactions (0.1 vol cDNA reactions) were heated to 95° C. twice and subjected to PCR using the same primers and conditions as those described for tail DNA amplification. PCR cycles were as follows: 94° C. for 5 min, 40 cycles of 94° C. (1 min), 55° C. (2 min), and 72° C. (3 min), and a final elongation at 72° C. for 10 min. PCR products were electrophoresed, blotted, and probed with a 0.76 kbp BamHI fragment of the rat CRF gene, which includes the amplified region.

In Situ Hybridization and Immunohistochemistry

Mice were anesthetized and perfused with saline, followed by 4% paraformaldehyde in 0.1 M borate buffer. Brains and peripheral tissues were stored overnight at 4° C. in fixative containing 10% sucrose. Frozen sections (30 μm thick) were stored in antifreeze solution [30% polyethylene glycol, 20% glycerol, and 50% $NaPO_4$ (0.05 M)] until use. Tissue sections were mounted onto gelatin/poly-L-lysine-coated slides, and hybridizations were carried out using conditions previously described by [Imaki et al., supra]. [$^{35}$S]cRNA probes were synthesized using SP6 (antisense) and T7 (sense) primed synthesis from a prepro-CRF cDNA plasmid template. Oligonucleotide hybridizations were performed using a 42-mer complementary to the human GH fragment of the transgene:

5'-TTA-GGA-CAA-GGC-TGG-TGG-GCA-CTG-GAG-TGG-CAA-CTT-CCA-GGG3'; (SEQ ID NO:3)

Labeling and hybridization conditions using oligonucleotides were as follows. Oligonucleotides were 3'-end labeled using terminal deoxynucleotide transferase and [$_{35}$S]deoxy-ATP to a specific activity of $3 \times 10^8$ cpm/μg. Tissue sections were hybridized with $2.4 \times 10^6$ cpm at 42° C. in 50% formamide, 5×Denhardt's, 4×SSC (1×SSC=0.15 M NaCl, 0.015 M sodium citrate), 10% dextran sulfate, 20 mM phosphate, 60 mM dithiothreitol, 125 μg/ml salmon sperm DNA, and 140 μg/ml transfer RNA. Slides were washed at 55° C. in 1×SSC for 45 min, dipped in NTB3 nuclear track emulsion (1:1 with water; Eastman Kodak, Rochester, N.Y.), exposed for 8 days to 4 weeks, and developed. The sections were counterstained with thionin.

Pituitary sections (20 μm) from a transgenic mouse were incubated with rabbit α-CRF-(1-21) (code 207-195) at 1:375 for 48 h at 4° C., labeled with biotinylated donkey α-rabbit complexed with streptavidin-Texas red followed by sheep αACTH at 1:1000 for 1 h at room temperature, and labeled with donkey α-sheep fluorescein isothiocyanate. To determine if the CRF positive cells colocalized with gonadotropes, sections were incubated simultaneously with rabbit α-CRF-(1-21) and either mouse αLH at 1:500 or mouse αFSH at 1:1000 for 48 h at 4° C., and labeled with goat α-rabbit lissamine-conjugated rhodamine and goat α-mouse immunoglobulin G fluorescein isothiocyanate, respectively, for 1 h at room temperature.

Surgery and Intracerebroventricular (ICV) Microinjections

Mice were anesthetized with ketamine/xylazine (50 mg/kg, sc.) and mounted in a stereotaxic instrument with the incisor bar at −2.0 mm. Mice were implanted with a single cannula placed in the right lateral ventricle. Guide cannulae (26 gauge, Plastics One, Roanoke, Va.) were positioned 1.0 mm above the lateral ventricle (A/P at the bregma; D/V 1.4 mm below the surface of the skull and M/L 1.1 mm lateral). The cannulae were fixed to the skull using three 1.6 mm stainless steel screws and dental cement. Animals were allowed to recover from surgery for a minimum of 5 days before testing, during which time 33 gauge dummy cannulae were left inside the guide cannula. Intracerebroventricular infusions were performed using 33 gauge infusion cannulae cut to extend 1.0 mm beyond the end of the guide cannula. Dummy cannulae were removed and replaced by the infusion cannulae which were fitted to PE-50 tubing and connected to a 50 μl syringe. The infusion samples were delivered in a 2.0 μl volume over 30 sec. using an automated infusion pump. Infusion cannula were left in place for an additional 30 sec. to prevent efflux of infusion material and then replaced by the dummy cannulae for the duration of the experiment. To verify canulae placements, the brains were removed, fixed in 10% formalin/10% sucrose and frozen just prior to tissue sectioning on a freezing microtome.

Behavioral Tests

All behavioral tests were performed between 1900 and 2400 hours during the active period of these animals.

Elevated Plus Maze

A four arm radial maze consisting of two opposing enclosed arms (30 cm high×30 cm long×5 cm wide) and two opposing exposed arms (30 cm×5 cm) was elevated on a pedestal 30 cm above the surface of a table and situated in the center of a dimly lit room. Computer interfaced, infrared photocell beams situated around the perimeter and diagonally across the center of the maze monitored the amount of time spent in each compartment and provided a gross measure of overall activity. Mice were placed in the center of the maze facing an enclosed arm to begin the five minute test period and the apparatus was cleaned with wetted towels after each test. Tests involving brain cannula infusions were performed 5 minutes following the infusion of the test peptide or vehicle. The CRF antagonist, α-helical CRF 9-41 (available from American Peptide Inc., Sunnyvale, Calif.), was dissolved in acidified water (pH 6.7) and animals were infused with 1 or 5 μg of α-helical CRF 9-41 in a 2 μl volume or given vehicle alone (2 μl).

Novel Environment

A plexiglas box (33 cm long×23 cm wide×20 cm high) was equipped with computer interfaced, infrared photocell beams which trisected the length of the chamber. Mice which had not previously experienced this testing environment were allowed to explore the box for 30 minutes during which time horizonal locomotor activity as well as movement from one end of the box to the other was recorded. The boxes were cleaned with water following each use. Experiments designed to test the effect of social defeat stress were performed 3–5 minutes following exposure of the test animal to the stressor. The social defeat stress consisted of a brief encounter between a test male (intruder) and a resident male (resident) which has been housed with a family comprised of a female and pups. The resident-intruder interaction took place in the resident male cage and in all cases, the intruder was placed in the cage for <1 minute. At the first sign of aggressive behavior between the two animals, the intruder male was removed from the resident cage and housed singly for 3–5 minutes before placement into the novel environment chamber to measure locomotor activity.

Statistical Analysis

The overall two and three factor diagrams, as well as simple main effects, were statistically analyzed by ANOVA. Individual means (±SEM) were compared using Student's t-tests.

EXAMPLE 1

Generation of MT-CRF Transgenic Mice

To test whether CRF overproduction leads to chronic activation of pituitary ACTH production and excess glucocorticoid secretion, transgenic mice that overexpress CRF were developed. To avoid feedback regulation of CRF transgene expression, the murine MT-1 gene promoter was used in place of the natural CRF promoter [Durnam and Palmiter, J. Biol. Chem. Vol. 256:5712–5716 (1981)]. Because the polyadenylation signal sequence used in CRF transcription was not included in this clone, the 3'-untranslated region of the human GH gene, which contains a polyadenylation signal sequence, was included at the 3'-end of the CRF structural gene.

From 100 pups, 11 transgenic animals were identified by tail DNA dot blot analysis. Founder animals were expected to express abnormally high steady state levels of circulating CRF, leading to elevated ACTH release and increased adrenal corticosterone production. Elevated plasma corticosterone levels were found in six founder animals, suggesting that the CRF transgene was expressed in these animals, leading to adrenal overproduction of corticosterone. These founders displayed truncal obesity, with large adipose deposits, muscle wasting, bilateral symmetric hair loss, and abnormally transparent skin. The severity of these Cushingoid features and the degree of endocrine dysfunction varied widely among founders, without apparent correlation with transgene copy number. Treatment of the founder animals with zinc (25 mM $ZnSO_4$ in the drinking water) did not further raise the corticosterone levels in these animals.

Animals with increased corticosterone levels were selected for the generation of offspring. Animals in this line show physical changes that can be attributed to excess circulating corticosterone, such as hair loss, marked fat deposition, and thin skin [see Nelson in Endocrinology, DeGroot, ed., Saunders, Phila, Vol. 2:1660–1675 (1989)]. Transgenic lymphoid organs were markedly reduced in size, with a 3-fold difference noted in spleen weight and an approximately 2-fold difference in thymus weight. Increased adrenal weights were also a consistent finding among the transgenic animals.

Male transgenic mice bred successfully, while trangenic females showed decreased fertility. Reduced fertility may be due to elevated corticosterone levels or CRF levels in the brain, since both hormones have been shown to influence reproductive function [see, for example, Rivier & Vale, in Endocrinology Vol. 114:914–920 (1984); Rivier et al., in Science Vol. 231:607–609 (1986)].

EXAMPLE 2

Hypothalamic-Pituitary-Adrenal Axis Hormone Levels in MT-CRF Transgenics

Elevated levels of CRF were not detectable in peripheral blood of transgenics compared to littermate controls (See Durnam & Palmiter, supra.) To determine whether the increased synthesis of corticosterone in these animals was associated with elevated ACTH values, basal levels of ACTH and corticosterone were measured in serum obtained from offspring derived from a single lineage. In this transgenic line, ACTH values were 5-fold elevated compared with those in control nontransgenic animals. Such increases are well within the range capable of stimulating increased synthesis and secretion of corticosterone from the adrenal glands [see Rivier et al., in Endocrinology Vol. 110:272–278 (1982)]. Corticosterone levels in transgenic offspring were approximately 10-fold greater than baseline control (nontransgenic) values. The increases in ACTH most likely account for the observed increase in corticosterone.

Because the negative regulation of ACTH expression by glucocorticoids may attenuate pituitary responsiveness to chronic CRF stimulation, plasma ACTH levels were determined in the absence of glucocorticoid feedback. Plasma ACTH levels among adrenalectomized transgenics and controls (nontransgenic) were markedly elevated, as expected in a setting devoid of glucocorticoid suppression, but showed no significant difference between the two groups. This finding may indicate that in the absence of glucocorticoid, CRF levels in normal and transgenic mice are sufficiently high to drive maximal ACTH production. Interestingly, transgenic mice reverted to a normal phenotype with respect to hair and skin changes within several weeks postadrenalectomy, during which time circulating corticosterone remained at undetectable levels.

EXAMPLE 3

Tissue Distribution of MT-CRF Transgene Expression

Because the transgenic animals exhibited elevated plasma ACTH levels without detectable increases in plasma CRF, the tissue distribution of CRF gene expression was determined. RNA expression of endogenous CRF in sites outside of the central nervous system has been observed at very low levels in rat testes and adrenal tissue [see Thompson et al., in Mol. Endocrinology Vol. 1:363–370 (1987)]. Of the peripheral tissues examined by Northern blot analysis, only transgenic testes contained CRF mRNA. Such limited tissue distribution was unexpected, since the majority of MT promoter-regulated transgenes have been reported to be transcribed in liver of kidney. Nevertheless, CRF expression was undetectable in kidney and liver in four distinct transgenic lines with Cushing's syndrome, even in the presence of zinc induction. Mapping of CRF expression within the testes by in situ hybridization using a rat CRF probe revealed hybridization signal over seminiferous tubules and in an interstitial pattern consistent with Leydig cell expression. Both germ cells and Leydig cells have been reported to produce CRF in normal animals [see Fabbri and Dufau, supra; see also Yoon et al., in Endocrinology Vol. 122:759–761 (1988)]. Further analysis of CRF expression using reverse transcriptase PCR amplification with transgene-specific primers revealed expression in testes consistent with the Northern blot analyses, and in addition, a positive signal was seen in adrenal, heart, and weakly in lung using this more sensitive detection system. Examination of RNAs isolated from several brain sites showed transgene expression in pituitary, hypothalamus, and preoptic area of transgenic brain. To avoid false amplification of the transgene from potential genomic DNA contamination in the RNA samples, all samples were treated twice with DNAse. In addition, cDNA reactions were performed in the presence and absence of reverse transcriptase before PCR amplification.

EXAMPLE 4

Localization of CRF Expression in Transgenic Mouse Brains

In situ hybridization using a rat CRF probe showed that transgenic animals have elevated signals for CRF mRNA in nearly all areas of expression shared in common with controls. In addition, several regions not previously identified as sites of CRF gene or peptide expression contained robust mRNA signals, such as the arcuate nucleus of the hypothalamus, the subfornical organ, the lateral habenula, the granule cell layer of the dentate gyrus, the dorsal subiculum, and the deep nuclei of the cerebellum. In contrast to the robust expression of CRF mRNA elsewhere in the central nervous system, the strength of the hybridization signal in the paraventricular nucleus of the hypothalamus was equivalent, or only marginally elevated, in transgenic animals compared to that in controls. Because the rat CRF probe does not distinguish between endogenous mouse and rat does not distinguish between endogenous mouse and rat transgene CRF expression, a transgene-specific oligonucleotide probe was used to verify that the CRF transgene was expressed in regions where high levels or ectopic regions of CRF expression has been observed. Although the hybridization signal obtained with the oligonucleotide probe is less than that observed using the rat CRF riboprobe due to the lowered sensitivity of this method, the transgene is clearly detectable in transgenic brains and absent in control non-transgenic animals. The transgene-specific oligonucleotide probe revealed a hybridization pattern similar to that detected by the rat gene CRF probe, suggesting that the regions of heightened expression and ectopic sites were due in part to the transgene. Moreover, the fact that the transgene appears to be expressed in the paraventricular nucleus of the hypothalamus, a major site of CRF expression in normal animals, provides a potential source of CRF overexpression that could stimulate ACTH production in transgenic animals. In addition, the transgenic animals displayed CRF mRNA and peptide in the pituitary. The positive cells represent approximately 5% of the pituitary cell population. Double immunofluorescence experiments showed that this expression does not colocalize with corticotropes; approximately 25% of these cells colocalized with FSH-positive cells, indicating partial overlap with gonadotropes [see Borrelli et al., in Nature Vol. 339:538–541 (1989)]. CRF-positive terminals were also observed in the posterior lobe of pituitaries, which is consistent with the CRF expression seen in magnocellular neurons of the paraventricular and supraoptic nuclei and provides an additional source of CRF that could contribute to the elevated ACTH levels in transgenic mice.

EXAMPLE 5

Evaluation of Animal Behavior

Behavior of the CRF transgenics differed markedly from control animals in test situations designed to assess behavioral activation and anxiety states. For example, CRF transgenic mice exhibit increased emotionality, consistent with the known anxiogenic effects of centrally administered CRF. This behavioral anxiety may result from a chronic state of CRF overproduction, a condition that occurs throughout development and the adult life span of these animals. Behavioral alterations were observed in both the elevated plus-maze and in a novel environment paradigm. These effects appear to be due to central CRF expression since pre-treatment with the CRF antagonist, α-helical CRF 9-41, reversed the state of anxiety of transgenic animals.

Figure 1A:
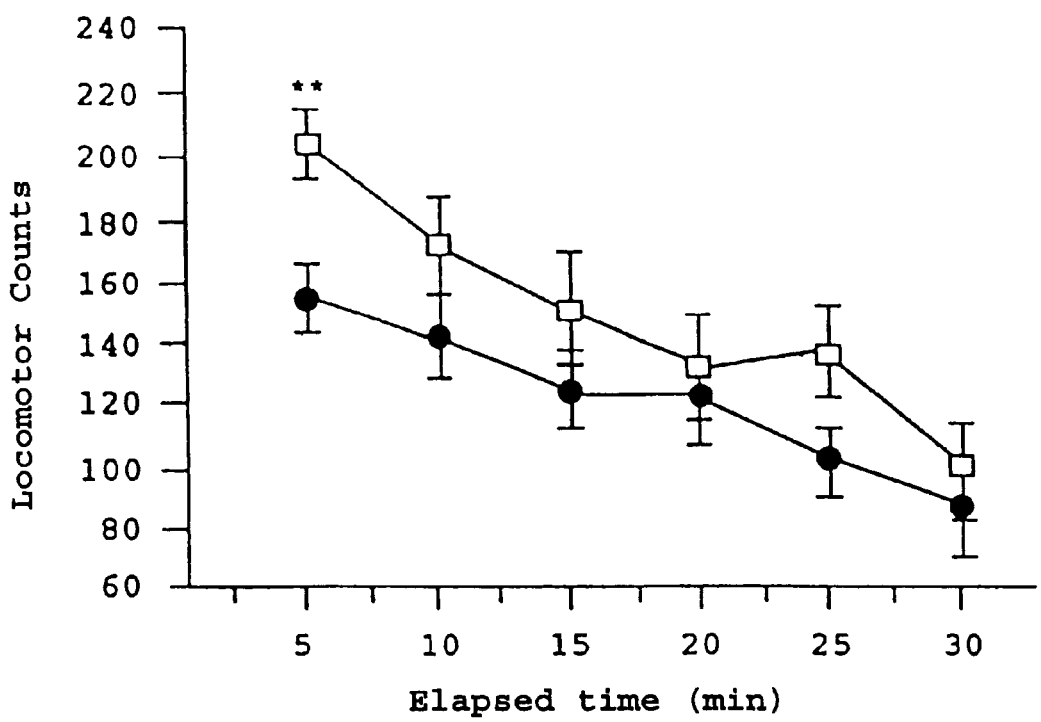
FIGS. 1A and 1B present the mean (±SEM) locomotor activity (FIG. 1A) and crossover frequency (FIG. 1B) of control (□; n=10) and transgenic CRF (●; n=12) mice placed individually for 30 minutes in novel photocell cages. * $p<0.05$; ** $p<0.01$.
Figure 1B:
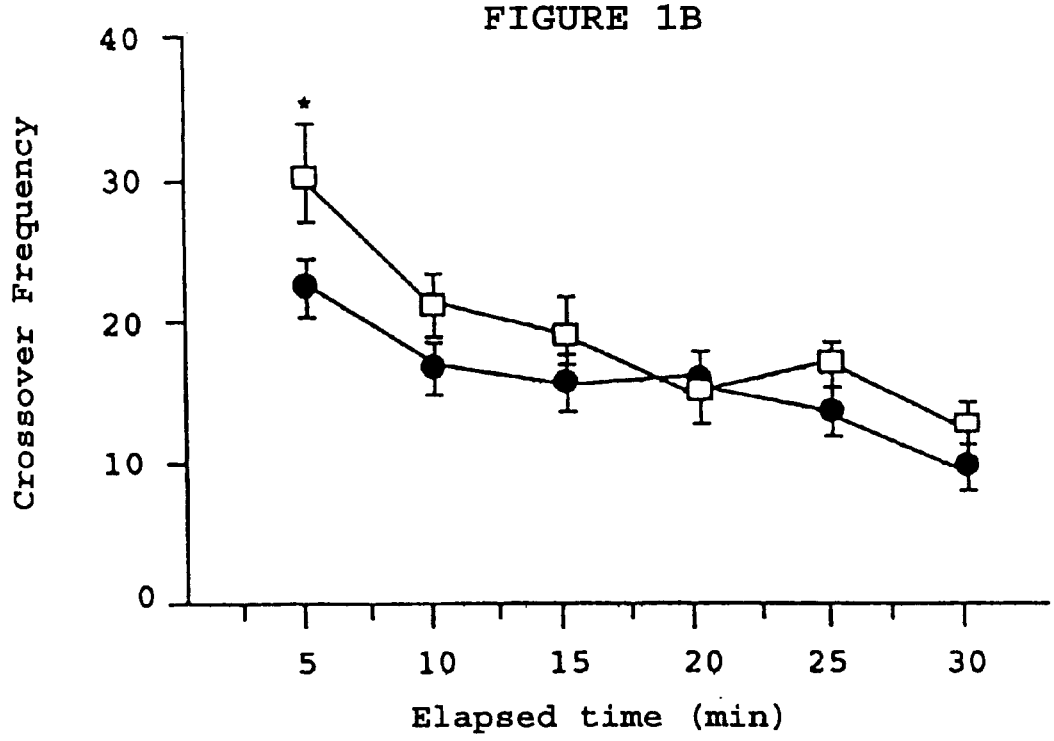

For example, in the "novel environment" test, locomotor activity varied significantly $[F(5,100)=25.73, p<0.001]$. Analysis of simple effects indicated that CRF transgenic mice were less active and produced fewer crossovers during the first five minutes of the test $[F(1,20)=9.43, p<0.006); F(1,20)=4.35, p<0.05)]$ bud did not differ significantly from nontransgenic littermate controls at any subsequent five minute interval up to 30 minutes (see FIG. 1).

Figure 2:
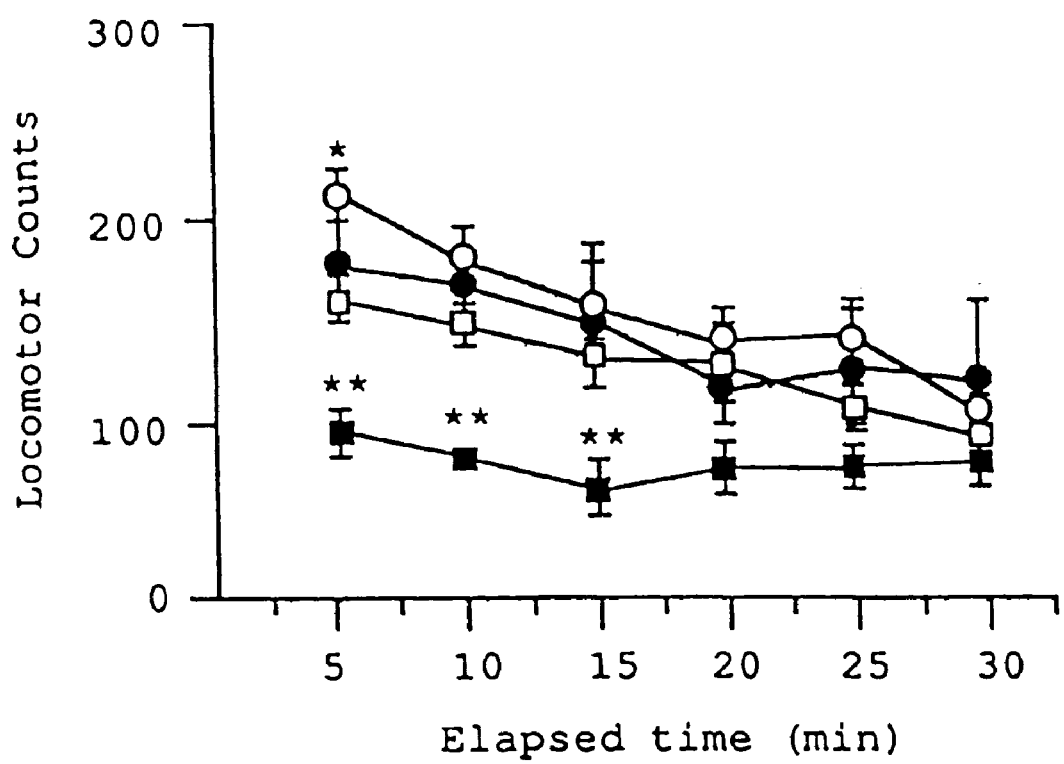
FIG. 2 presents the mean (±SEM) locomotor activity of untreated control (○; n=10) or CRF transgenic (□; n=12)

Assessment of locomotor activity in the "novel environment" test showed a clear reduction in locomotion among transgenic animals compared to controls. To test whether this behavioral difference could be exaggerated by social defeat stress, animals were tested in the novel environment immediately following social defeat by an aggressive male counterpart mouse. A significant effect was observed during the first 15 minutes of testing wherein transgenic animals were markedly hypoactive compared with unstressed transgenics (see FIG. 2). CRF transgenics exposed to this social stress were also found to be significantly less active than control animals exposed to the same stressor.

The percentage of time spent on exposed vs. enclosed arms $[F(1,16)=4.56, p<0.05]$ and the overall activity $[F(1, 16)=7.53, p<0.02]$ were significantly reduced among CRF transgenic mice relative to controls (see FIG. 3).

The behavior of animals in the novel setting has been shown to be sensitive to the effects of acute, central administration of CRF (Sutton et al., supra; Sherman and Kalin, supra). These effects are known to occur in the absence of HPA activation (Britton et al, supra; Britton et al., supra). The CRF transgenic animals represent an animal model wherein the transgene is apparently not subject to the regulatory controls of the endogenous CRF gene and thus are under continuous CRF stimulation. Elevated CRF expression is accompanied by a marked suppression in locomotor activity when tested in a novel environment, a finding that parallels the novelty dependent hypoactivity following central CRF infusion. This transient reduction in exploration is probably not a motor deficit since the locomotor activity of transgenic and littermate control mice did not differ following the initial five minute measurement interval. Furthermore, the groups did not differ over the latter part of the measurement interval in crossover frequency, a measure of ambulation from one end of the testing environment to the other, suggesting that the activity observed resulted from a normal pattern of exploration. Thus, among the CRF transgenics, continuous exposure to centrally derived CRF results in a behavioral pattern similar to the anxiogenic-like effects of acute CRF administration.

In order to investigate whether the behavioral effects of novelty could be potentiated in the invention animal model by pre-exposure to a supplemental psychological stressor, the effect of a social defeat stressor upon locomotor activity in the novel environment was tested. The locomotor hypoactivity of the CRF transgenics compared with control animals subjected to the same compound stressor was severe and more persistent than that induced by novelty alone. These results indicate that CRF transgenics display an exaggerated response to stress which is consistent with an increased state of emotionality.

The behavioral effects of central CRF injection in a variety of paradigms have been shown to be anxiogenic [Dunn and Berridge, Brain Res. Rev. Vol. 15:71–100 (1990)]. An elevated plus-maze has been employed herein as a validated animal model of anxiety. This test, which is based on the natural aversion of rodents to open spaces, is sensitive to the effects of both anxiolytic and anxiogenic agents in rats and mice [Pellow et al., supra; Lister, supra; Onaivi et al., J. Pharm. Exp. Ther. Vol. 253:1002–1009 (1990)] and to the stress-protective effects of a CRF antagonist [Heinrichs et al., Brain Res. Vol. 581:190–197 (1992)]. As in the novel environment, clear group differences were observed between the CRF transgenics and control animal using this test paradigm. The percentage of time spent on the exposed vs. enclosed arms was significantly reduced among the transgenics compared with control animals, suggesting that the invention animal model exhibits a spontaneous state of anxiety.

EXAMPLE 6

Effect of ICV Administration of CRF Antagonist on the Elevated Plus-Maze

To test whether increased emotionality in invention transgenics was due, at least in part, to the expression of CRF in these transgenics, the CRF antagonist, α-helical CRF 9-41, was infused into the lateral ventricles prior to testing in the elevated plus-maze.

The reduced time spent on the open arms in vehicle-treated CRF transgenic mice relative to vehicle-treated controls (t(12)=1.8, p<0.05 one-tailed) was completely reversed by ICV infusion of the CRF antagonist, α-helical CRF 9-41, at a dose of 5 μg [F(1,12)=17.2, p<0.005] but not 1 μg, five minutes prior to testing on the elevated plus maze (see FIG. 4A). Among vehicle-treated CRF transgenic mice, the overall activity score in the Elevated plus maze was suppressed relative to vehicle-treated controls [t(12)=1.97, p<0.5 one-tailed] while neither 1 nor 5 μg doses of α-helical CRF 9-41 altered activity significantly relative to the respective vehicle-treated groups (see FIG. 4B).

Administration of a 5 μg dose of the antagonist reversed the significant decrease in the percentage of time spent on the exposed vs. enclosed arms characteristic of the transgenic mice. These findings support the hypothesis that CRF overproduction in this animal model leads to increased emotionality.

EXAMPLE 7

Cannulae Placement Histology

Brains from 60% of the cannulated animals were fixed and histologic sections were examined to determine the general accuracy of cannula placement. Of those examined, 81% exhibited correct cannula placement with the needle tract extending through the corpus callosum into the right lateral ventricle. The accuracy of cannula placements among those examined suggests that the present results employing CRF antagonist can be attributed to infusion into the lateral ventricle.

While the invention has been described in detail with reference to certain preferred embodiments thereof, it will be understood that modifications and variations are within the spirit and scope of that which is described and claimed.

That which is claimed is:

1. A transgenic mouse whose genome comprises a DNA sequence comprising a rat corticotropin releasing factor (CRF) gene operably linked to a mouse metallothionein (MT) promoter, wherein said mouse expresses said gene encoding rat CRF in the paraventricular nucleus of the hypothalamus at a level equivalent, or marginally elevated, as compared to endogenous levels of mouse CRF in the paraventricular nucleus of the hypothalamus of a wild-type mouse, and wherein expression levels of said gene encoding rat CRF are sufficient to effect phenotypic changes consistent with Cushing's disease and anxiety in said mouse.

2. A transgenic mouse according to claim 1, wherein said mouse further expresses said gene encoding rat CRF in a plurality of tissues of the central nervous system in which a wild-type mouse does not express endogenous mouse CRF.

3. A transgenic mouse according to claim 1, wherein said mouse further expresses said gene encoding rat CRF in the seminiferous tubules of said mouse.

4. A transgenic mouse acccording to claim 1, wherein said mouse produces a higher level of adrenocortocotrophic hormone (ACTH) than a wild-type mouse.

5. A transgenic mouse according to claim 1, wherein said mouse produces a higher level of corticosterone than a wild-type mouse.

6. A transgenic mouse according to claim 1, wherein said mouse is a model for Cushing's disease.

7. A transgenic mouse according to claim 1, wherein said mouse is a model for behavioral anxiety.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: Other nucleic acid;
      (A) DESCRIPTION: Oligonucleotide (xi) SEQUENCE DESCRIPTION: SEQ ID NO:1:

ACAGGAAACT GATGGAGATT ATC      23

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: Other nucleic acid;
      (A) DESCRIPTION: Oligonucleotide (xi) SEQUENCE DESCRIPTION: SEQ ID NO:2:

TGGTGGGCAC TGGAGTGGCA ACT      23

(2) INFORMATION FOR SEQ ID NO:3:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: Other nucleic acid;
      (A) DESCRIPTION: Oligonucleotide (xi) SEQUENCE DESCRIPTION: SEQ ID NO:3:

TTAGGACAAG GCTGGTGGGC ACTGGAGTGG CAACTTCCAG GG      42